United States Patent [19]

Antwiler

[11] Patent Number: 5,141,486
[45] Date of Patent: Aug. 25, 1992

[54] WASHING CELLS

[75] Inventor: Glen D. Antwiler, Lakewood, Colo.

[73] Assignee: Cobe Laboratories, Inc., Lakewood, Colo.

[21] Appl. No.: 609,748

[22] Filed: Nov. 5, 1990

[51] Int. Cl.5 .......... B01D 43/00; B04B 11/00
[52] U.S. Cl. .......... 494/37; 494/27; 494/35
[58] Field of Search .......... 494/37, 27, 23, 35, 494/36, 22, 25, 26, 43, 64; 210/781, 782, 360.1, 369; 604/4, 5, 6

[56] References Cited

U.S. PATENT DOCUMENTS 4,668,214  5/1987  Reeder ................... 494/37
4,684,361  8/1987  Feldman et al. .

Primary Examiner—Robert W. Jenkins

[57] ABSTRACT

Red blood cells being salvaged are centrifuged into a liquid layer, mixed with a wash solution, and thereafter separated therefrom.

9 Claims, 1 Drawing Sheet

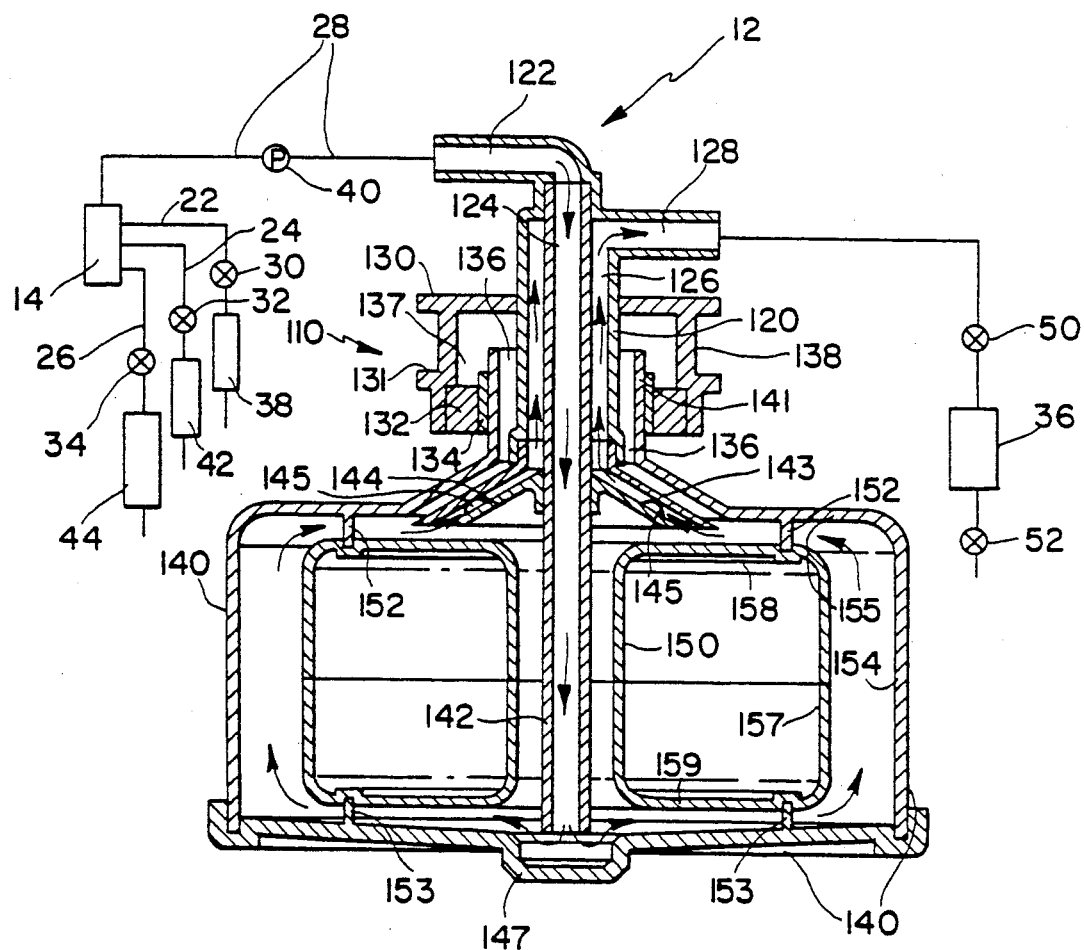

WASHING CELLS

FIELD OF THE INVENTION

This invention relates to washing cells, and in particular to washing red blood cells that have been formed in a centrifuge into a fluid layer.

BACKGROUND OF THE INVENTION

It is known to salvage an individual's blood by collecting it with suction, centrifuging it to form a layer of red blood cells, washing under centrifugation the layer with saline to remove plasma and impurities such as heparin, and returning it to the same individual (i.e., an "autologous" salvage). A centrifuge bowl useful in such salvage is disclosed in Feldman et al. U.S. Pat. No. 4,684,361, "Centrifuge", granted Aug. 4, 1987, and hereby incorporated herein by reference; a tubing set useful in such salvage and including a centrifuge bowl generally in accordance with Feldman et al. has been sold by Cobe Laboratories, Inc., assignee hereof, under the trademark BRAT.

SUMMARY OF THE INVENTION

I have discovered that improved washing of cells results if they are intermediately in centrifugation brought together in dispersed form with a volume of wash liquid.

In preferred embodiments, a centrifuged layer of red blood cells is formed, is washed under centrifugation with a saline solution to remove plasma and other centrifuged-out materials, is transferred to a container with a volume of wash saline greater than the red blood cell layer volume, is agitated therewith, is retransferred as a mixture to centrifuge the wash liquid therefrom, is given a further saline wash under centrifugation, and is then transferred to a reinfusion bag.

PREFERRED EMBODIMENT

Disclosure of the presently preferred embodiment of the invention follows:

DRAWINGS

The figure is a partially diagrammatic view of an apparatus for practicing the invention.

STRUCTURE

There is shown in the figure a centrifuge bowl 140, in a tubing set, indicated generally at 12 (not to scale), useful in the invention.

Centrifuge bowl 140 is a part of tubing set 12. A tubing set as disclosed, as well as equipment in which to mount and use it in a prior art method as well as the method of the present invention, is sold by applicant's assignee, Cobe Laboratories, Inc., under the trademark BRAT. Tubing set 12 includes manifold 14, which communicates with blood collection reservoir line 22, saline bag line 24, and blood reinfusion bag line 26. Manifold 14 is connected by tubing 28 with centrifuge inlet 122. Valving 30, 32, 34 for selectively opening and closing tubing 22, 24, and 26 is carried by the cooperating equipment above referred to, in which the centrifugation set 12 is mounted in use.

Set 12 also includes waste collection bag 36, which is supplied through outlet 128 of centrifuge 110, and which is hung in use on the above-mentioned equipment; this equipment also rotatively drives bowl 140. Valves 50, 52 are slide clamps, as well known in the art.

The set 12 does not as supplied actually include reservoir 38 and saline bag 42; and reinfusion bag 44 is not connected up as supplied, although included in the set package.

METHOD

In the presently preferred embodiment, bowl 140, which holds about 250 ml. in its portions not occupied by spacer 150 and inlet downspout 142, is spun empty on the BRAT equipment above referred to to a rotational velocity of 4400 rpm, following which blood to be salvaged is introduced from a blood collection reservoir 38 (rigid polycarbonate, of 3-liter volume, into which is moved blood that has been salvaged from the patient and processed as known in the art) carried by the equipment above referred to, through valve 30, line 22, manifold 14, peristaltic pump 40, and lines 28 into inlet 122, and bowl 140 until a fluid red blood cell layer forms on the inner surface of bowl 140 to a thickness such that there is left adjacent the outer periphery of spacer 150 a gap about ⅛ inch in radial distance. In the preferred embodiment gap size is monitored automatically using a reflective color sensor to sense red blood cell layer surface location. During this period plasma and impurities such as heparin and hemoglobin emerge into bag 36 through centrifuge bowl outlet 128. Depending on the hematocrit of the blood in the collection reservoir feeding the centrifuge, for example, 700 ml. of blood is introduced into the centrifuge, to produce a roughly 150 ml. layer of fluid, predominately red blood cells, with most of the remaining volume of centrifuged blood going into bag 36.

The red blood cell layer is then washed with 200 ml. of "saline" (in the preferred embodiment a 0.9% solution in water of NaCl), which is pumped through line 24 (valve 32 controlling flow therethrough, being now open, and that controlling flow through line 22 being now closed), manifold 14, line 28, pump 40, and inlet 122, from saline bag 42 carried by the above-mentioned equipment, and which has a volume capacity of 1000 ml., but which contains before pumping from it the 200 ml. wash portion just mentioned only 800 ml. of saline, pumping and washing being done with the bowl still spinning at full speed, some of the wash liquid effluent moving on then into bag 36.

The reversible-direction pump 40 carried by the above-mentioned equipment cooperates with line 28 to selectively pump in either direction therethrough.

Centrifuge bowl 140 is then stopped, the pumping direction of pump 40 reversed, and the fluid red blood cell material, no longer a layer upon stopping of the centrifuge, but descending into the bottom of bowl 140, and which has a volume of about 150 ml., is pumped, along with about 100 ml. of saline, still in the bowl, through line 28, manifold 14, line 24, and valve 32 into saline bag 42, at a rate causing turbulence, for mixing. Agitation for mixing there is further provided by pumping in, following the red blood cells, 100 ml. of air.

Bowl 140 is then rotated again at 4400 rpm, and the entire contents of saline bag 42 introduced thereinto, pump 40 pumping direction having been reversed again. A new red blood cell liquid layer results, and excess, lighter, fluid again goes off into bag 36.

The now-empty saline bag 42 is replaced by a fresh saline bag 42 containing a full 1000 ml. of saline. With the bowl still spinning, a further 200 ml. wash for the red blood cell layer exterior is provided, effluent moving into bag 36.

Valve 32 is then closed; centrifuge bowl 140 rotation is then stopped; valve 34 is then opened; and the pumping direction of pump 40 again reversed, and the red blood cell layer dropped in the bowl and pumped through manifold 14, line 26, and valve 34 into reinfusion bag 44, which may then be given to a medical attendant for re-introduction into the patient.

The centrifugation set 12 may if desired be used for multiple sequences according to the invention. Waste bag 36 may suitably have a volume of 10 liters, and serve for several sequences. That bag or reinfusion bag 44 (volume 1 liter in the preferred embodiment) may be replaced if desired, as is preferably, as seen, saline bag 42. The tubing in the preferred embodiment is preferably ¼ inch ID, except that the tubing to and from waste bag 36 downstream of valve 50 is preferably slightly larger in ID.

The method of the invention provides blood of improved freedom from undesired impurities, as compared with prior art methods of attempting to purify centrifuged layers of red blood cells.

OTHER EMBODIMENTS

Other embodiments of the invention will occur to those skilled in the art. Thus, just as examples, salvage need not be autologous. The intermediate uncentrifuged wash step need not be done in the saline bag. Radial gap adjacent the red blood cell layer surface may be regulated manually.

What is claimed is:

1. The method of removing impurities from red blood cells which comprises:

centrifuging blood containing said impurities to form a red blood cell layer also containing said impurities, stopping said centrifuging, mixing red blood cells from said layer with a wash solution during said stopping, and centrifuging the resultant mixture to remove said wash solution.

2. The method of claim 1 which includes the further step of washing said layer with a wash solution prior to said stopping said centrifuging.

3. The method of claim 1 which includes the further step of washing a second red blood cell layer resulting from said centrifuging the resulting mixture with a wash solution while centrifuging said second red blood cell layer.

4. The method of claim 1 in which the volume of said wash solution is in excess of the volume of said red blood cell layer.

5. The method of claim 4 in which the volume of said wash solution is four times the volume of said red blood cell layer.

6. The method of claim 1 which includes the further steps of washing said layer with a wash solution prior to said stopping said centrifuging and washing a second red blood cell layer resulting from said centrifuging the resulting mixture with a wash solution while centrifuging said second red blood cell layer, the volume of each said wash solution being in excess of the volume of each said red blood cell layer.

7. The method of claim 1 in which said wash solution is a dilute solution of sodium chloride and in which said mixing step includes moving said red blood cells from said layer into a container for said wash solution.

8. The method of claim 7 in which said mixing step includes agitation of said cells relative to said wash solution.

9. The method of claim 1 in which said red blood cells of said layer are removed from a centrifuge bowl and thereafter mixed with said wash solution.

* * * * *

REEXAMINATION CERTIFICATE (2790th)

United States Patent [19]

Antwiler

[11] B1 5,141,486

[45] Certificate Issued Jan. 30, 1996

[54] WASHING CELLS

[75] Inventor: Glen D. Antwiler, Lakewood, Colo.

[73] Assignee: Cobe Laboratories, Inc., Lakewood, Colo.

Reexamination Request:
No. 90/003,656, Dec. 7, 1994

Reexamination Certificate for:
Patent No.: 5,141,486
Issued: Aug. 25, 1992
Appl. No.: 609,748
Filed: Nov. 5, 1990

[51] Int. Cl.[6] .................................................. B01D 43/00
[52] U.S. Cl. .............................. 494/37; 494/27; 494/35
[58] Field of Search ................... 494/27, 37, 23, 494/25, 36, 22, 26, 43, 64, 85, 35; 210/781, 782, 360.1; 604/4, 5, 6; 422/44

[56] References Cited

U.S. PATENT DOCUMENTS

| | | | |
|---|---|---|---|
| 3,347,454 | 10/1967 | Bellamy, Jr. et al. | 233/14 |
| 3,452,924 | 7/1969 | Schlutz | 233/14 |
| 3,982,691 | 9/1976 | Schlutz | 233/2 |
| 4,007,871 | 2/1977 | Jones et al. | 233/27 |
| 4,010,894 | 3/1977 | Kellogg et al. | 233/27 |
| 4,049,192 | 9/1977 | Krebs et al. | 233/14 |
| 4,076,169 | 2/1978 | Schlutz | 233/14 |
| 4,094,461 | 6/1978 | Kellogg et al. | 233/27 |
| 4,157,780 | 6/1979 | Larrabee | 233/14 |
| 4,482,342 | 11/1984 | Lueptow et al. | 494/21 |
| 4,850,995 | 7/1989 | Tie et al. | 604/6 |
| 5,053,121 | 10/1991 | Schoendorfer et al. | 210/90 |

FOREIGN PATENT DOCUMENTS

| | | |
|---|---|---|
| 2587495 | 9/1985 | France . |
| 56-28540 | 7/1981 | Japan . |
| 62-19177 | 1/1987 | Japan . |
| 1-230521 | 9/1989 | Japan . |

*Primary Examiner*—Robert Jenkins

[57] ABSTRACT

Red blood cells being salvaged are centrifuged into a liquid layer, mixed with a wash solution, and thereafter separated therefrom.

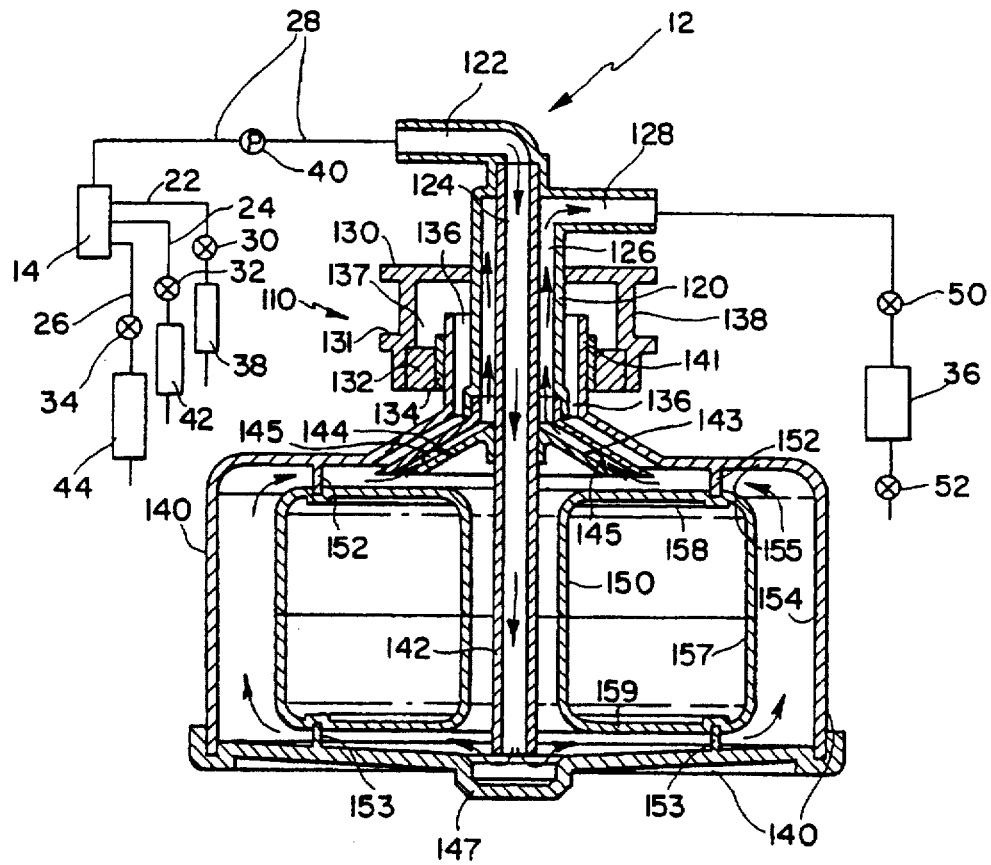

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 5, 6 and 9 are determined to be patentable as amended.

Claims 3, 7 and 8, dependent on an amended claim, are determined to be patentable.

New claims 10–27 are added and determined to be patentable.

1. The method of removing impurities from red blood cells which comprises:

providing *a batch of* blood containing said impurities to a centrifuge, centrifuging *said batch of* blood containing said impurities *within said centrifuge* to form a red blood cell layer also containing said impurities, *wherein said centrifuging step comprises exposing said blood to centrifugal forces,* stopping said centrifuging *step, wherein said red blood cell layer is free from exposure to centrifugal forces,* mixing red blood cells from said *red blood cell* layer with a wash solution during said stopping *step to form a resultant mixture, said wash solution being for removing at least a portion of said impurities from said red blood cells,* and centrifuging [the] *said* resultant mixture to remove said wash solution *from said red blood cell layer.*

2. The method of claim 1 which includes the further step of washing said layer with a wash solution prior to said stopping said centrifuging *step, wherein at least a portion of said wash solution for said washing step comprises at least a portion of said wash solution for said mixing step.*

4. The method of claim 1 in which [the] *a* volume of said wash solution *used in said mixing step* is in excess of [the] *a* volume of said red blood cell layer.

5. The method of claim 4 in which [the] *said* volume of said wash solution is *at least* four times [the] *said* volume of said red blood cell layer.

6. The method of claim 1 which includes the further steps of washing said *red blood cell* layer with a *first* wash solution prior to said stopping said centrifuging *step* and washing a second red blood cell layer resulting from said centrifuging [the resulting] *said resultant* mixture *step* with a *second* wash solution while centrifuging said second red blood cell layer, the volume of each said wash solution being in excess of the volume of each said red blood cell layer.

9. The method of claim 1 in which said red blood cells of said *red blood cell* layer are removed from [a] *said* centrifuge [bowl] and thereafter mixed with said wash solution.

*10. The method of claim 1, further comprising the step of terminating said providing step, wherein at least a portion of said centrifuging step is performed after said terminating step.*

*11. The method of claim 10, wherein said centrifuge is rotating during said providing step.*

*12. The method of claim 1, wherein said centrifuging said blood, stopping, mixing, and centrifuging said resultant mixture steps are all performed for said batch and after a completion of said providing step.*

*13. The method of claim 1, wherein said red blood cell layer is within said centrifuge during at least a portion of said stopping step.*

*14. The method of claim 26, wherein a volume of said wash solution used in said mixing step is in excess of a volume of each said red blood cell layer.*

*15. The method of claim 1, wherein said mixing step comprises pumping said red blood cells together with said wash solution at a rate to induce turbulence within said red blood cells and said wash solution.*

*16. The method of claim 1, wherein said mixing step comprises pumping air into said red blood cells and said wash solution.*

*17. The method of claim 27, wherein said mixing step comprises pumping said red blood cells and said wash solution out of said centrifuge and into a container at a rate to induce turbulence within said red blood cells and said wash solution.*

*18. The method of claim 17, wherein said mixing step comprises pumping air into said red blood cells and said wash solution.*

*19. The method of claim 18, wherein said pumping air step is initiated only after said red blood cells and said wash solution are within said container.*

*20. The method of claim 17, wherein said container has a quantity of a wash solution before said pumping step.*

*21. The method of claim 1, wherein said stopping step comprises terminating a rotation of said centrifuge.*

*22. The method of claim 1, wherein said impurities comprise plasma.*

*23. The method of removing impurities from red blood cells which comprises:*

*centrifuging blood containing said impurities within a centrifuge to form a red blood cell layer also containing said impurities;*

*washing said red blood cell layer with a wash solution to remove said impurities from said red blood cell layer during said centrifuging step;*

*stopping said centrifuging step with said red blood cell layer and at least a portion of said wash solution remaining within said centrifuge during at least a portion of said stopping step;*

*removing red blood cells of said layer and said at least a portion of said wash solution from said centrifuge;*

*mixing said red blood cells from said layer with said at least a portion of said wash solution to form a resultant mixture during said stopping step;*

*providing said resultant mixture to a centrifuge; and*

*centrifuging said resultant mixture to remove wash solution from said red blood cells by separating said red blood cells from said wash solution.*

*24. The method of claim 23, wherein said centrifuging step comprises rotating said centrifuge and wherein said stopping step comprises terminating a rotation of said centrifuge.*

*25. The method of claim 23, wherein said centrifuging step comprises exposing said blood to centrifugal forces and wherein during said stopping step said red blood cell layer is free from exposure to centrifugal forces.*

26. The method of claim 1 which includes the further steps of washing said red blood cell layer with a first wash solution prior to said stopping said centrifuging step and washing a second red blood cell layer resulting from said centrifuging said resultant mixture step with a second wash solution while centrifuging said second red blood cell layer, wherein at least a portion of said first wash solution for said washing step comprises at least a portion of said wash solution for said mixture step.

27. The method of claim 1 in which said red blood cells of said red blood cell layer are removed from said centrifuge during at least a portion of said stopping step.

* * * * *